(12) United States Patent
Hatano et al.

(10) Patent No.: US 6,309,666 B1
(45) Date of Patent: Oct. 30, 2001

(54) PHARMACEUTICAL PREPARATION IN FORM OF COATED CAPSULE RELEASABLE AT LOWER PART OF DIGESTIVE TRACT

(75) Inventors: Harumi Hatano, Amagasaki; Takahiro Ito, Yao; Takashi Ishibashi, Sakai; Hiroyuki Yoshino, Suita; Masakazu Mizobe, Takatsuki, all of (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 08/680,753

(22) Filed: Jul. 15, 1996

(30) Foreign Application Priority Data

Jul. 20, 1995 (JP) .................................................. 7-183655

(51) Int. Cl.$^7$ ...................................................... A61K 9/52
(52) U.S. Cl. .......................... 424/463; 424/457; 424/494; 424/496; 424/497; 514/772.3; 514/781; 514/782; 514/784
(58) Field of Search ................................... 424/463, 474, 424/479, 480, 482, 490, 494, 497, 481, 496, 457

(56) References Cited

U.S. PATENT DOCUMENTS

| 4,012,444 | * | 3/1977 | Lunts et al. | 260/559 S |
| 4,910,021 | * | 3/1990 | Davis et al. | 424/456 |
| 5,217,720 | * | 6/1993 | Sekigawa et al. | 424/480 |
| 5,468,503 | | 11/1995 | Yamada et al. | 424/461 |
| 5,654,004 | | 8/1997 | Okayama et al. | 424/479 |

FOREIGN PATENT DOCUMENTS

| 0 425 699 | 5/1991 | (EP) . |
| 62-99322 | 5/1987 | (JP) . |
| 4264022 | 9/1992 | (JP) . |
| 624962 | 2/1994 | (JP) . |
| 710745 | 1/1995 | (JP) . |
| 6-256166 | 9/1996 | (JP) . |
| 9410983 | 5/1994 | (WO) . |

OTHER PUBLICATIONS

Ishino, Ryuzo et al., "Design and Preparation of Pulsatile Release Tablet as a New Oral Drug Delivery System." Chemical Pharmaceutical Bulletin, vol. 40, No. 11, pp. 3036–3041 (1992).

Theeuwes, F. et al., "Systems for Triggered, Pulsed, and Programmed Drug Delivery.", Annals New York Academy of Sciences, vol. 618, pp. 428–440 (1991).

Saffran, Murray et al., "A New Aproach to the Oral Administration of Insulin and Other Peptide Drugs.", Science, vol. 233, pp. 1081–1084 (1986).

* cited by examiner

Primary Examiner—James M. Spear
(74) Attorney, Agent, or Firm—Browdy and Neimark

(57) ABSTRACT

A pharmaceutical preparation in the form of a coated capsule which can release contents of a capsule at a lower part of the digestive tract comprising (a) a hard capsule containing at least an acidic substance, (b) a polymer film soluble at low pH which is formed on a surface of said hard capsule, and (c) an enteric coating film which is formed on a surface of said polymer film soluble at low pH. According to the pharmaceutical preparation of the present invention, any kind of a medicament can be delivered to any desired site between the upper part of the small intestine and the lower part of the large intestine in the digestive tract by controlling the amount of polymer(s) used for the polymer film soluble at low pH and/or by selecting the kind of the polymer film soluble at low pH and/or the acidic substance without any complicated requirements for each medicament.

12 Claims, 9 Drawing Sheets

PHARMACEUTICAL PREPARATION IN FORM OF COATED CAPSULE RELEASABLE AT LOWER PART OF DIGESTIVE TRACT

BACKGROUND OF THE INVENTION

The present invention relates to a pharmaceutical preparation which can release contents of a capsule at a lower part of the digestive tract and more particularly to a pharmaceutical preparation in the form of a coated capsule by which contents of a capsule can be selectively delivered to a desired site, e.g. the large intestine, and quickly released thereat.

Selective delivery of a medicament to the large intestine has been desired in drug therapies, for instance, a local therapy for inflammatory disease in the digestive tract such as ulcerative colitis or Crohn's disease, or an oral administrative therapy with a medicament of a peptide which is apt to be decomposed chemically or enzymatically in the digestive tract, with a medicament of which the absorption site is limited, or with other medicament.

In order to efficiently realize the site-selective delivery of a medicament to the large intestine, it is necessary to design a pharmaceutical preparation taking into account the physical and physiological environment in the human digestive tract and the residence time of the pharmaceutical preparation in the digestive tract. With respect to the physical and physiological environment in the digestive tract, it is recognized that the value of pH in the stomach is usually 1.8 to 4.5 in a healthy human and that the value of pH in the intestines is 6.5 to 7.5. According to the results of the widespread research of Davis et al., the residence time of a pharmaceutical preparation in the human stomach is 0.5 to 10 hours. Further not only is the inter-individual variation of the residence time large, but also the residence time is considerably influenced, for example, by feeding, the size of the pharmaceutical preparation to be administered and the like. On the other hand, the passage time of a pharmaceutical preparation through the small intestine is generally recognized to be 3±1 hours and the inter- and intra-individual variation is relatively small (Journal of Controlled Release, 2, 27–38 (1985)).

With respect to a method by which a medicament can be selectively released at the large intestine, hitherto various researches have been done. There have been proposed a pharmaceutical preparation which is obtained by coating a sustained release pharmaceutical preparation with an enteric coating (Annals of the New York Academy of Science, 618, 428–440 (1991)), a pharmaceutical preparation utilizing a technique for controlling the starting time of the release (Chemical & Pharmaceutical Bulletin, 40, 3036–3041 (1992), European Patent Publication No. 0425699 and Japanese Unexamined Patent Publication No. 256166/1994), a pharmaceutical preparation in the form of tablet which is obtained by coating insulin with an azopolymer soluble at the large intestine (Saffran et al, Science, 233, 1081–1084 (1986)) and the like, as well as pharmaceutical preparations using known techniques such as an enteric pharmaceutical preparation and a sustained release pharmaceutical preparation.

However, every conventional method has a problem such as insufficient site-selectivity, poor practicality due to peculiarity of the material to be used or complicated process for manufacturing a preparation.

For instance, as the enteric pharmaceutical preparation starts to release a medicament abruptly at the upper part of the small intestine, a selective delivery of the medicament can not be achieved.

When using the sustained release pharmaceutical preparation, a considerable amount of a medicament is released while the pharmaceutical preparation stays in the stomach and passes through the small intestine because the medicament is continuously released.

Furthermore, attempts have been made to suppress the release of a medicament in the stomach by coating a sustained release pharmaceutical preparation with an enteric coating. However, the problem that the medicament is released during the passage of the pharmaceutical preparation through the small intestine, has not entirely been solved by the above-mentioned enteric-coated sustained release pharmaceutical preparation.

The conventional pharmaceutical coated preparation requires optimization of, for example, a combination of a medicament and a coating agent, a coating amount, a kind of a solvent for a coating liquid, a spraying condition, a drying condition and the like, for every medicament to be used. In the case of a medicament which is easily decomposed by heating or by a solvent to be used, the optimization requires much labor.

Furthermore, there are some cases where the obtained optimum conditions are not always applicable to another medicament, in fact, the cases where the conditions are not applicable are numerous compared with cases where applicable. Therefore, it is hard to say that the conventional pharmaceutical preparation is excellent in a wide use.

Additionally, before coating, the conventional pharmaceutical coated preparation essentially requires processes such as granulation process, shieving process and tabletting process. Thus, it takes more time, labor and cost.

An object of the invention is to provide a pharmaceutical preparation which is excellent in a site-selective delivery. In particular the object of the invention is to provide a pharmaceutical preparation whereby medicaments, pharmaceutical preparations, functional substances or the like contained in a hard capsule can be delivered to any desired site of the lower part of the digestive tract.

A still further object of the invention is to provide a pharmaceutical preparation in the form of a coated capsule wherein any kind of medicaments etc. can be commonly or widely used without a special formulation.

These and the other objects of the present invention will become apparent from the description hereinafter.

SUMMARY OF THE INVENTION

It has now been found that (i) a hard capsule containing an acidic substance which is firstly coated with a substance soluble at low pH and further coated with an enteric substance, can quickly release contents of the hard capsule at any desired site between the upper part of the small intestine and the lower part of the large intestine according to the kind of the acidic substance and the kind of and the amount of the substance soluble at low pH, and (ii) only if using such a capsule, there can be obtained a pharmaceutical preparation whereby any kind of a medicament, a pharmaceutical preparation, a functional substance or the like can be delivered and quickly released at any desired site between the upper part of the small intestine and the lower part of the large intestine in the digestive tract.

In accordance with the present invention, there is provided a pharmaceutical preparation in the form of a coated capsule which can release contents of a capsule at a lower part of the digestive tract comprising (a) a hard capsule containing at least an acidic substance, (b) a polymer film soluble at low pH which is formed on a surface of said hard capsule, and (c) an enteric coating film which is formed on a surface of said polymer film soluble at low pH.

The pharmaceutical preparation of the present invention relates to a hard capsule for delivering the contents to the lower part of the digestive tract. That is, the pharmaceutical preparation of the present invention has the following characteristics: When a pharmaceutical preparation stays in the stomach, an enteric coating film protects the pharmaceutical preparation. Successively when the preparation transits from the stomach to the upper part of the small intestine, the enteric coating film dissolves and starts to disappear. Then, the digestive juice gradually penetrates through a low pH-soluble polymer film and a hard capsule to enter the hard capsule, and thereby an acidic substance is dissolved. The solution having low pH which is produced by the dissolution of the acidic substance, dissolves the hard capsule and the low pH-soluble polymer film, resulting in disappearance thereof. Then, the contents of the hard capsule such as medicaments, pharmaceutical preparations and functional substances are quickly released.

Accordingly, the releasing rate of the contents of the hard capsule does not substantially vary with the kind of a hard capsule, the kind or amount of polymer(s) used for a low pH-soluble polymer film or the kind of an acidic substance, and it takes about 1 hour after the start of release to release 80% of the contents of the hard capsule.

The hard capsule in the pharmaceutical preparation of the present invention is quickly dissolved by a solution having low pH which is produced by the dissolution of the acidic substance. Therefore, the pharmaceutical preparation of the present invention has the characteristic that the lag-time, the time period from the discharge of the pharmaceutical preparation from the stomach till the contents of the hard capsule start to be released, can be controlled to any length by selecting the kind and/or amount of polymer(s) used for a low pH-soluble polymer film and/or the kind of the acidic substance.

Thus, the pharmaceutical preparation of the present invention has an advantage that the contents of the hard capsule can be released quickly and at any desired site of the lower part of the digestive tract.

In addition, a conventional pharmaceutical preparation soluble at the lower part of the digestive tract can be obtained only after the complicated determination of conditions taking into account various processes such as granulation and tabletting, protection of a medicament in the stomach and the upper part of the small intestine, disintegration property in the large intestine, loss of a medicament during preparing a pharmaceutical preparation and the like.

However, the pharmaceutical preparation of the present invention has remarkable advantage that there is no need of the complicated determination of conditions. Namely, according to the present invention, it is not required to determine conditions for the purpose of e.g. protection of a medicament etc. in the process of preparing a pharmaceutical preparation after a medicament etc. is filled into a hard capsule because the medicament etc. to be delivered to the lower part of the digestive tract is filled into a hard capsule.

DETAILED DESCRIPTION

Figure 1:
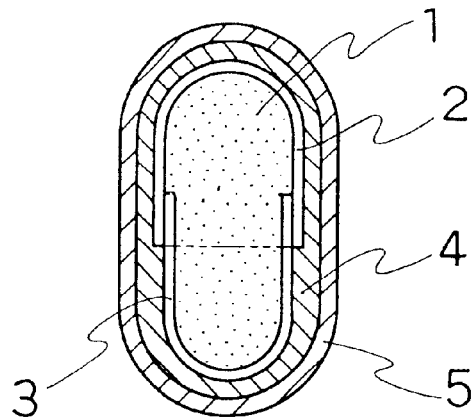
FIG. 1 shows a sectional view of an embodiment of the pharmaceutical preparation of the present invention.

In the present invention, the term "lower part of the digestive tract" means a part from the duodenum as the upper part of the small intestine, via the jejunum, the ileum, the cecum, the ascending colon, the transverse colon, the descending colon and the sigmoid colon, to the rectum.

According to the pharmaceutical preparation of the present invention, contents of a capsule such as a medicament, a pharmaceutical preparation or a functional substance can be selectively released at any desired site of the lower part of the digestive tract as mentioned above. In order to effectively exhibit the characteristic of the present invention, preferably contents of a capsule are released at any desired site between the jejunum and the rectum, more preferably at any desired site between the ileum and the rectum, much more preferably at any desired site of the large intestine between the cecum (the ostium ileocecale) and the rectum. Most preferably, contents of a capsule are released at any desired site of the ascending colon, the transverse colon, the descending colon or the sigmoid colon.

With respect to the hard capsule used in the present invention, any type of hard capsule suitable for oral administration can be used without any limitation, and preferably a commercially available hard capsule is used in view of simplification of the preparation process. Examples of the hard capsule are, for instance, a gelatin capsule such as CONI-SNAP capsule (trade name, commercially available from CAPSUGEL AG, Japan), a corn starch capsule such as CAPILL (trade name, commercially available from Warner-Lambert Company, U.S.A.), a hydroxypropylmethylcellulose capsule such as HPMC capsule (trade name, commercially available from Japan ELANCO CO. LTD., Japan) and the like. Among these, a gelatin capsule and a hydroxypropylmethylcellulose capsule are preferable, and a gelatin capsule is more preferable from a view point of its good dissolution pattern.

The hard capsule in the present invention may be in various types.

A size of the hard capsule is not particularly limited. Preferable capsules have a size of Size No. 2, No. 3 and No. 4 described in the 12th Japanese Pharmacopoeia (hereinafter also referred to as JP XII) in view of handling.

The acidic substance to be contained in the hard capsule used in the present invention is a solid substance of which aqueous solution has pH value of at most 5. The form of the acidic substance is not particularly limited and the acidic substance in various forms such as crystal, powder and granule can be used.

Examples of the acidic substance are, for instance, an organic acid such as succinic acid, maleic acid, tartaric acid, citric acid, fumaric acid or malic acid and an inorganic acid such as boric acid. These acidic substances may be used alone or in the combination of one or more kinds thereof. A preferable acidic substance is an organic acid such as succinic acid, maleic acid, tartaric acid, citric acid, fumaric acid or malic acid, and particularly succinic acid is preferable, due to its good physical and chemical stability, etc.

An acidic substance to be contained in a hard capsule can be a medicament if the medicament is acidic.

The amount of the acidic substance to be contained in the hard capsule is not particularly limited and may be an enough amount to dissolve the polymer film soluble at low pH (hereinafter also referred to as "low pH-soluble polymer film") which is formed around the hard capsule. The optimum amount of the acidic substance can be easily determined by carring out the dissolution test.

The term "low pH" means pH ranging from pH 1 to pH 5, preferably from pH 1 to pH 3.

The polymer soluble at low pH used for the low pH-soluble polymer film in the pharmaceutical preparation of the present invention can be a film-formable polymeric substance which is soluble at the acidic range of from pH 1 to pH 5 but not soluble at the neutral and alkali ranges of a pH of higher than 5. Accordingly, a polymer usually used as a gastric-soluble polymer in this pharmaceutical field can be suitably used. Examples of the low pH-soluble polymer are, for instance, polyvinyl acetal diethylaminoacetate, methyl methacrylate-butyl methacrylate-dimethylaminoethyl methacrylate copolymer such as Eudragit E100 (trade name, commercially available from Röhm Pharma, Germany), polyvinyl aminoacetal and the like. These polymers soluble at low pH can be used alone or in admixture thereof. Among these, polyvinyl acetal diethylaminoacetate and methyl methacrylate-butyl methacrylate-dimethylaminoethyl methacrylate copolymer are preferable because these polymers are frequently used in the actual pharmaceutical production.

The enteric polymer used for the enteric coating film in the pharmaceutical preparation of the present invention can be a film-formable polymeric substance which is soluble in an aqueous medium of a pH of higher than 5 but not soluble in an aqueous medium of a pH of at most 5. The enteric polymer used in the present invention includes, for instance, a cellulose derivative, an acrylic copolymer, a maleic copolymer, a polyvinyl derivative, shellac and the like.

The examples of the cellulose derivative are, for instance, hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate and the like. Among them, hydroxypropylmethylcellulose acetate succinate, hydroxypropylmethylcellulose phthalate and carboxymethylethylcellulose are preferable. Further, hydroxypropylmethylcellulose acetate succinate is more preferable.

The examples of the acrylic copolymer are, for instance, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer such as Eudragit L100, Eudragit S or Eudragit S100 (each being trade name, commercially available from Röhm Pharma, Germany), methacrylic acid-ethyl acrylate copolymer such as Eudragit L100-55 (trade name, commercially available from Röhm Pharma, Germany), methyl acrylate-methacrylic acid-octyl acrylate copolymer, and the like. Among them, methacrylic acid-methyl methacrylate copolymer is preferable.

The examples of the maleic copolymer are, for instance, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer and the like.

The examples of the polyvinyl derivative are, for instance, polyvinyl alcohol phthalate, polyvinyl acetal phthalate, polyvinyl butylate phthalate, polyvinyl acetoacetal phthalate and the like.

In the pharmaceutical preparation of the present invention, the above-mentioned enteric polymer may be used alone or in the combination of one or more kinds thereof.

Among the above-mentioned enteric polymers, the cellulose derivative and the acrylic copolymer are preferable. Particularly, the cellulose derivative is preferable.

The mechanism in the pharmaceutical preparation of the present invention is as follows: When a pharmaceutical preparation stays in the stomach, an enteric coating film protects the pharmaceutical preparation from dissolution. Successively when the preparation transits from the stomach to the upper part of the small intestine, the enteric coating film dissolves and starts to disappear. Then, the digestive juice gradually penetrates through a low pH-soluble polymer film and a hard capsule to enter the hard capsule, and thereby an acidic substance is dissolved. The solution having low pH which is produced by the dissolution of the acidic substance, dissolves the hard capsule and the low pH-soluble polymer film, resulting in disappearance thereof. At this time, the contents of the hard capsule are quickly released.

Accordingly, the pharmaceutical preparation of the present invention makes it possible for contents of a hard capsule to be selectively released at any desired site of the lower part of the digestive tract by controlling the amount of polymer(s) used for a low pH-soluble polymer film and by selecting the kind of a low pH-soluble polymer and an acidic substance.

The time period from the discharge of the pharmaceutical preparation from the stomach till contents of the hard capsule start to be released in the intestine (hereinafter referred to as "lag-time") can be determined by controlling the amount of polymer(s) used for a low pH-soluble polymer film and by selecting the kind of a low pH-soluble polymer and an acidic substance. For example, when the amount of polymer(s) used for a low pH-soluble polymer film is increased or decreased, the lag-time becomes long or short.

The general passage time of a pharmaceutical preparation through the small intestine is recognized to be 3±1 hours. Therefore, when the lag-time is adjusted to be about 2 hours, about 4 hours and about 7 hours, there can be obtained pharmaceutical preparations of the present invention from which the contents of the hard capsule would be released approximately at the lower part of the ileum, the ascending colon and the transverse colon, respectively. When the longer lag-time is determined, there can be obtained a pharmaceutical preparation from which the contents of the hard capsule would be released approximately at the lower part of the large intestine.

The pharmaceutical preparation of the present invention is suitably designed so that contents of a hard capsule cannot substantially be released during the length of time corresponding to the desired lag-time when the dissolution test is carried out with the JP 2nd-Fluid (JP XII) according to the dissolution test (paddle method) described in the 12th Japanese Pharmacopoeia (JP XII).

Each amount of the low pH-soluble polymer film and the enteric coating film is not particularly limited.

A suitable amount of the low pH-soluble polymer film varies with the length of the predetermined lag-time and the combination of the components. A suitable amount of the enteric coating film may be an amount in the extent that the contents of a hard capsule are not released in the stomach. These amounts can easily be determined by carrying out the dissolution test. In general, it is preferable that the amount of the low pH-soluble polymer film is determined to be from 5 to 500% by weight and the amount of the enteric coating film is determined to be from 10 to 400% by weight, based on the weight of the hard capsule itself (empty capsule).

As the combination of each polymer of the low pH-soluble polymer film and the enteric coating film in the present invention, the low pH-soluble polymers and the enteric polymers as mentioned above are selected and used with taking into account the predetermined lag-time, the properties of the hard capsule, the kind of the acidic substance and the like.

Examples of preferable combinations of each polymer of the low pH-soluble polymer film and the enteric coating film in the present invention are shown in Table 1, and examples of preferable combinations of each concrete polymer thereof in Table 2.

TABLE 1

| No. | Polymer of the low pH-soluble polymer film | Polymer of the enteric coating film |
|---|---|---|
| 1 | Polyvinyl acetal diethylaminoacetate | Enteric cellulose derivative |
| 2 | Polyvinyl acetal diethylaminoacetate | Shellac |
| 3 | Polyvinyl acetal diethylaminoacetate | Enteric acrylic copolymer |
| 4 | Polyvinyl acetal diethylaminoacetate | Enteric maleic copolymer |
| 5 | Polyvinyl acetal diethylaminoacetate | Enteric polyvinyl derivative |
| 6 | Methyl methacrylate-butyl methacrylate-dimethylaminoethyl methacrylate copolymer | Enteric cellusloe derivative |
| 7 | Methyl methacrylate-butyl methacrylate-dimethylaminoethyl methacrylate copolymer | Shellac |

TABLE 1-continued

| No. | Polymer of the low pH-soluble polymer film | Polymer of the enteric coating film |
|---|---|---|
| 8 | Methyl methacrylate-butyl methacrylate-dimethylaminoethyl methacrylate copolymer | Enteric acrylic copolymer |
| 9 | Methyl methacrylate-butyl methacrylate-dimethylaminoethyl methacrylate copolymer | Enteric maleic copolymer |
| 10 | Methyl methacrylate-butyl methacrylate-dimethylaminoethyl methacrylate copolymer | Enteric polyvinyl delivative |

TABLE 2

| No. | Polymer of the low pH-soluble polymer film | Polymer of the enteric coating film |
|---|---|---|
| 11 | Polyvinyl acetal diethylaminoacetate | Hydroxypropylmethyl-cellulose acetate succinate |
| 12 | Polyvinyl acetal diethylaminoacetate | Hydroxypropylmethyl-cellulose phthalate |
| 13 | Polyvinyl acetal diethylaminoacetate | Carboxymethylethyl-cellulose |
| 14 | Polyvinyl acetal diethylaminoacetate | Methacrylic acid-methyl methacrylate copolymer |
| 15 | Methyl methacrylate-butyl methacrylate-dimethylaminoethyl methacrylate copolymer | Hydroxypropylmethyl-cellulose acetate succinate |
| 16 | Methyl methacrylate-butyl methacrylate-dimethylaminoethyl methacrylate copolymer | Hydroxypropylmethyl-cellulose phthalate |
| 17 | Methyl methacrylate-butyl methacrylate-dimethylaminoethyl methacrylate copolymer | Carboxymethylethyl-cellulose |
| 18 | Methyl methacrylate-butyl methacrylate-dimethylaminoethyl methacrylate copolymer | Methacrylic acid-methyl methacrylate copolymer |

A medicament, a pharmaceutical preparation, a functional substance or the like may be contained in the hard capsule in the pharmaceutical preparation of the present invention.

The medicament to be contained in the hard capsule is not particularly limited as long as it is orally administerable. Examples of such medicaments are, for instance, chemotherapeutic agents, antibiotics, respiratory stimulants, antitussives, expectorants, antimalignanttumor agents, autonomic agents, psychotropic agents, local anesthetics, muscle relaxants, agents affecting the digestive organs, antihistamines, toxicopetic agents, hypnotics, sedatives, antiepileptics, antipyretics, analgesics, antiinflammatory agents, cardiotonics, antiarrhythmic agents, diuretics, vasodilators, antilipemic agents, nutrients, tonics, alteratives, anticoagulants, agents for liver disease, hypoglycemics, antihypertensives and the like.

Particularly, it is beneficial to use a medicament which locally acts on the large intestine, a medicament which is desired to be absorbed at the large intestine for the reason that the medicament is quickly degradated at the small intestine, and the like.

The pharmaceutical preparation to be contained in the hard capsule is not particularly limited as long as it is orally administerable. Examples of such pharmaceutical preparations are, for instance, powder, fine granule, granule, tablet, oily suspensions and the like. These pharmaceutical preparations may have a controlled release property such as sustained release property.

The functional substance to be contained in the hard capsule is a substance which has no pharmacological action but exerts a favorable influence in vivo. Examples of the functional substance are, for instance, useful enterobacterium like lactobacillus, calcium polycarbophil which swells in the large intestine to facilitate the defecation, and the like. The functional substance may not be a single substance. For example, to the above-mentioned calcium polycarbophil, there can be added e.g. cellulose, a sodium carboxymethyl starch such as Exprotab (trade name, commercially available from Kimura Sangyo Co., Ltd., Japan), a pretreated starch such as Starch 1500 (trade name, commercially available from Japan Colorcon Ltd., Japan) and the like.

In the case that a medicament and an acidic substance are contained in a hard capsule, the medicament is filled into the capsule in the state that the chemical stability of the medicament and the acidic substance can be assured during storage for a long period. The form of both components and the method for filling them etc. are not particularly limited. For instance, after mixing a medicament and an acidic substance in the form of crystal or powder as it is, the resulting mixture may be filled into a hard capsule, or the resulting mixture may be granulated and the granule is formed into powder, fine granule, granule or tablet and filled into a hard capsule. Alternatively, for the purpose of avoiding interaction between a medicament and an acidic substance, each material in the form of crystal or powder may be separately layered using a partition layer to prevent direct contact of both materials and, after preparing tablets of a medicament and an acidic substance separately, the tablets may be filled into a hard capsule. As to the partition, any substance which does not cause an unfavorable effect on the pharmaceutical preparation of the present invention can be used for the material of the partition, and, for instance, an excipient etc. which are usually used in this field can be used.

In the case that a functional substance is contained in a hard capsule, the filling of the functional substance can be carried out in the same way as in the case of a medicament.

In the pharmaceutical preparation of the present invention, an intermediate layer comprising at least one member selected from the group consisting of a medicament and a water-soluble substance can be provided between the low pH-soluble polymer film and the enteric coating film, if desired.

Providing an intermediate layer comprising a water-soluble substance may make it possible to prevent the possible alteration of the characteristic of the low pH-soluble polymer film which occurs in forming the enteric coating film. The medicament contained in the intermediate layer may be the same or different from a medicament which can be contained in the hard capsule.

Examples of the medicament usable for the intermediate layer are not particularly limited as long as it is an orally administrable medicament as cited above. Examples of the water-soluble substance usable for the intermediate layer are, for instance, a water-soluble polymeric substance, e.g. a water-soluble polysaccharide ether such as methylcellulose, hydroxypropylcellulose or hydroxypropylmethylcellulose (for example, TC-5 (trade name, commercially available from Shin-Etsu Chemical Co., Ltd.)), a water-soluble polyvinyl derivative such as polyvinylpyrrolidone or polyvinylalcohol, a polysaccharide such as pullulan, a polyethyleneglycol etc.; a saccharide, e.g. a monosaccharide such as glucose, a disaccharide such as sucrose etc.; a low molecular electrolyte, e.g. an inorganic salt such as sodium chloride etc.; and the like.

It is preferable that the amount of the intermediate layer is determined to be from 8 to 320% by weight, in particular, from 16 to 80% by weight, based on the weight of the hard capsule itself (empty capsule).

The method for preparing the pharmaceutical preparation of the present invention is not particularly limited and the general method known to a person skilled in the art can be used. The form of the acidic substance and contents of the hard capsule may be crystal, powder, fine granule, granule, tablet and the like. For example, a hard capsule containing a medicament can be prepared by mixing an acidic substance and a medicament together with an excipient, a binder, a lubricant and the like and by preparing a granule from the resulting mixture according to the general method such as wet granulation or dry granulation and then by filling the granule into a hard capsule.

The coating of the low pH-soluble polymer film, the enteric coating film and an intermediate layer between the low pH-soluble polymer film and the enteric coating film can be carried out according to the method usually used in this field by means of HICOATER (trade name, made by Freund Industrial Co., Ltd., Tokyo, Japan), a pan coating apparatus, a centrifugal fluidizing type granulating and coating apparatus or the like. Both aqueous coating methods and non-aqueous coating methods generally used in this field can be employed for the above-mentioned coating.

As to a coating solution, examples of the solvent used for the coating solution are, for instance, an alcohol such as methyl alcohol, ethyl alcohol, n-propyl alcohol, isopropyl alcohol, n-butyl alcohol, 2-methoxyethanol (trade name: Methyl cellosolve, commercially available from KATAYAMA CHEMICAL INDUSTRIES CO., LTD., Japan) or 2-ethoxyethanol (trade name: Cellosolve, commercially available from KATAYAMA CHEMICAL INDUSTRIES CO., LTD., Japan); a hydrocarbon such as hexane, cyclohexane, petroleum ether, petroleum benzine, ligroin, benzene, toluene or xylene; a ketone such as acetone or methyl ethyl ketone; a hydrocarbon halide such as dichloromethane, chloroform, carbon tetrachloride, ethylene dichloride, trichloroethylene or 1,1,1-trichloroethane; an ester such as methyl acetate, ethyl acetate or butyl acetate; an ether such as isopropyl ether or dioxane; water; and the like.

Among the above-mentioned solvents, a solvent to be used can be selected according to a property of each coating layer and can suitably be used in admixture thereof. Among these examples, particularly an alcohol, a hydrocarbon halide, a ketone, water and the like are preferable, and concretely ethyl alcohol, acetone, water and the like are preferable.

In the pharmaceutical preparation of the present invention, a sealing means can be provided around a joint of a body and a cap of the hard capsule. By providing a sealing means, there can be obtained an excellent pharmaceutical preparation which has a little variation of the lag-time between each pharmaceutical preparation.

A sealing agent used for the sealing means can be a substance which can make the surface of the hard capsule at the joint of a body and a cap smooth. Examples of the sealing agent are, for instance, a water-soluble polymer, an water-insoluble polymer, a low pH-soluble polymer, an enteric polymer, a saccharide, a low molecular electrolyte and the like.

As the water-soluble polymer used as the sealing agent, there can be used water-soluble polymers which can be used for the intermediate layer. Examples of the water-soluble polymer are, for instance, a water-soluble polysaccharide ether such as methylcellulose, hydroxypropylcellulose or hydroxypropylmethylcellulose; a water-soluble polyvinyl derivative such as polyvinylpyrrolidone or polyvinylalcohol; a polysaccharide such as pullulan; a polyethyleneglycol; and the like.

Examples of the water-insoluble polymer used as the sealing agent are, for instance, a water-insoluble acrylic copolymer, e.g. ethyl acrylate-methyl methacrylate-trimethylammoniumethyl methacrylate chloride copolymer such as Eudragit RS or Eudragit RL (each being trade name, commercially available from Röhm Pharma, Germany), ethyl acrylate-methyl methacrylate copolymer such as Eudragit NE (trade name, commercially available from Röhm Pharma, Germany) and the like; a water-insoluble cellulose derivative such as ethylcellulose or cellulose acetate; a water-insoluble polyvinyl derivative such as polyvinyl acetate or polyvinyl chloride; and a mixture thereof.

As the low pH-soluble polymer used as the sealing agent, there can be used polymers soluble at low pH which can be used in the low pH-soluble polymer film in the present invention, for instance, polyvinylacetal diethylaminoacetate and the like.

As the enteric polymer used as the sealing agent, there can be used enteric polymers which can be used in the enteric coating film in the present invention, for instance, hydroxypropylmethylcellulose acetate succinate, methacrylic acid-methyl methacrylate copolymer, methacrylic acid-ethyl acrylate copolymer and the like.

As the saccharide and the low molecular electrolyte used as the sealing agent, there can be used saccharides and low molecular electrolytes which can be used for the intermediate layer. Examples of the saccharide are, for instance, a monosaccharide such as glucose, a disaccharide such as sucrose, and the like, and examples of the low molecular electrolyte are, for instance, an inorganic salt such as sodium chloride, and the like.

The above-mentioned sealing agent can be used alone or in admixture thereof.

The sealing means can be provided by applying a solution obtained by dissolving the sealing agent in a solvent on the joint, using a capsule sealing machine such as The Mod. SL/M (trade name, made by MG 2 S.p.A., Italy) or HICAPSEAL 15 (trade name, made by Japan Elanco Co., Ltd., Japan) or using e.g. a pipet such as a Pasteur pipet and by drying, to seal the joint. The coating amount of the sealing means is from 0.16 to 16% by weight, preferably from 0.8 to 3.2% by weight, based on the weight of the hard capsule itself (empty capsule).

Examples of the solvent are the same as those of the coating solutions usable for the coating of the low pH-soluble polymer film, etc.

To each of the contents of the hard capsule, the sealing means, the low pH-soluble polymer film, the enteric coating film and the intermediate layer between the low pH-soluble polymer film and the enteric coating film, if necessary, there can be added various additives generally used in the art of pharmaceutical preparation, for instance, an excipient, a binder, a disintegrant, a lubricant, an aggregation-preventing agent, a coating auxiliary, a coloring agent, a masking agent, a plasticizer to improve the coating property and the film-formability etc., a surfactant, an antistatic agent, an additive for controlling transmittance of light, and the like.

Examples of the excipient are, for instance, a saccharide such as sucrose, lactose, mannitol or glucose, starch, partially pregelatinized starch, crystalline cellulose, calcium phosphate, calcium sulfate, precipitated calcium carbonate, hydrated silicon dioxide and the like.

Examples of the binder are, for instance, an oligosaccharide or sugar alcohol such as sucrose, glucose, lactose, maltose, sorbitol or mannitol; a polysaccharide such as dextrin, starch, sodium alginate, carrageenan, guar gum, arabic gum or agar; a natural high molecular substance such as tragacanth, gelatin or gluten; a cellulose derivative such as methylcellulose, ethylcellulose, sodium carboxymethylcellulose or hydroxypropylmethylcellulose; a synthetic polymer such as polyvinylpyrrolidone, polyvinyl alcohol, polyvinyl acetate, polyethyleneglycol, polyacrylic acid or polymethacrylic acid; and the like.

Examples of the disintegrant are, for instance, calcium carboxymethylcellulose, sodium carboxymethylstarch, corn starch, hydroxypropylstarch, partially pregelatinized starch, low-substituted hydroxypropylcellulose, polyvinylpyrrolidone, calcium cross-linked carboxymethylcellulose and the like.

Examples of the lubricant and the aggregation-preventing agent are, for instance, talc, magnesium stearate, calcium stearate, colloidal silicon dioxide, stearic acid, hydrated silicon dioxide, synthetic magnesium silicate, fine grain silicon oxide, starch, sodium lauryl sulfate, boric acid, magnesium oxide, a wax, a hydrogenated oil, a polyethyleneglycol, sodium benzoate and the like.

Examples of the coating auxiliary are, for instance, a hydrogenated oil such as K-3 WAX (trade name, commercially available from Kawaken Fine Chemicals Co., Ltd., Japan), stearic acid such as NAA-174 (trade name, commercially available from NOF Corporation, Japan), calcium stearate, a polyoxyl stearate such as NONION S-154 (trade name, commercially available from MATSUMOTO TRADING CO., LTD., Japan), magnesium stearate, cetanol such as NAA-44 (trade name, commercially available from NOF Corporation) and the like.

Examples of the coloring agent are, for instance, a food color, a lake, caramel, a carotene, an annatto, cochineal, iron sesquioxide, an opaque coloring agent OPALUX mainly made of a lake and syrup, and the like.

Concrete examples thereof are, for instance, a food color such as Food Red No. 2, Food Red No. 3, Food Yellow No. 4, Food Yellow No. 5, Food Green No. 3, Food Blue No. 1, Food Blue No. 2 or Food Purple No. 1, a food aluminum lake such as Food Red No. 2 aluminum lake, Food Red No. 3 aluminum lake, Food Yellow No. 4 aluminum lake, Food Yellow No. 5 aluminum lake, Food Green No. 3 aluminum lake, Food Blue No. 1 aluminum lake, Food Blue No. 2 aluminum lake or Food Purple No. 1 aluminum lake, an annatto (a natural color derived from *Bixa orellana* L.), carmine (aluminum carminate), a Pearl essence (the principal ingredient thereof is guanine) and the like.

Examples of the masking agent are, for instance, titanium dioxide, precipitated calcium carbonate, calcium secondary phosphate, calcium sulfate and the like.

Examples of the plasticizer are, for instance, a phthalic acid derivative such as diethyl phthalate, dibutyl phthalate or butyl phthalyl butyl glycolate, a silicone oil, triacetin, propylene glycol, a polyethyleneglycol and the like.

Examples of the surfactant are, for instance, a nonionic surfactant such as sorbitan sesquioleate, polyoxyethylene sorbitan monooleate, polyoxyethylene monostearate, glycerol monostearate, propylene glycol monolaurate, polyoxyethylene lauryl ether, polyoxyethylene cetyl ether or polyoxyethylene hydrogenated castor oil; an ionic surfactant such as sodium dodecyl sulfate or benzalkonium chloride; and the like.

Examples of the antistatic agent are, for instance, hydrated silicon dioxide, silicic acid and the like.

Examples of the additive for controlling transmittance of light are, for instance, titanium oxide, talc and the like.

These additives can be added in any amount and at any time within the scope of the knowledge usually used in the field of pharmaceutical preparation.

Figure 2:
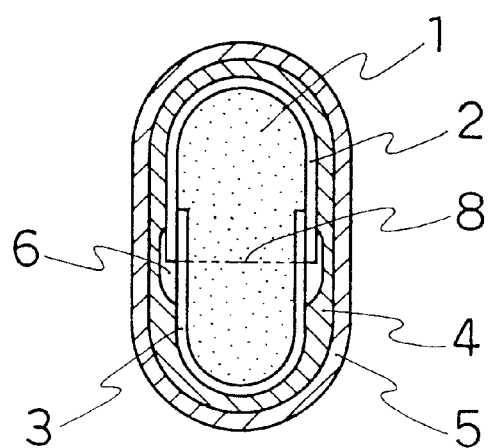
FIG. 2 shows a sectional view of another embodiment of the pharmaceutical preparation of the present invention wherein a sealing means is provided around the joint of the body and the cap of the hard capsule.
Figure 3:
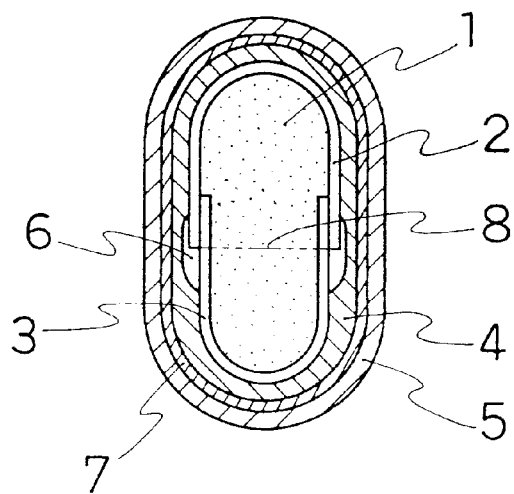
FIG. 3 shows a sectional view of another embodiment of the pharmaceutical preparation of the present invention wherein an intermediate layer is provided between the polymer film soluble at low pH and the enteric coating film.

As to the pharmaceutical preparation of the present invention, typical ones are shown in FIGS. 1 to 3.

In the pharmaceutical preparation of the present invention shown in FIG. 1, an acidic substance and, if desired, a medicament, a pharmaceutical preparation or a functional substance, 1 are contained in a hard capsule and the hard capsule is firstly coated with a low pH-soluble polymer film 4 and further coated with an enteric coating film 5.

In the pharmaceutical preparation of the present invention shown in FIG. 2, a sealing means 6 is provided around the joint 8 of the body 3 and the cap 2 in the hard capsule in the pharmaceutical preparation in FIG. 1. The joint 8 means a boundary of a connecting portion of the body 3 and the cap 2 of the hard capsule.

In the pharmaceutical preparation of the present invention shown in FIG. 3, a sealing means 6 is provided around the joint 8 in the hard capsule and an intermediate layer 7 comprising a medicament and/or a water-soluble substance is provided between the low pH-soluble polymer film 4 and the enteric coating film 5 in the pharmaceutical preparation in FIG. 1.

Figure 4:
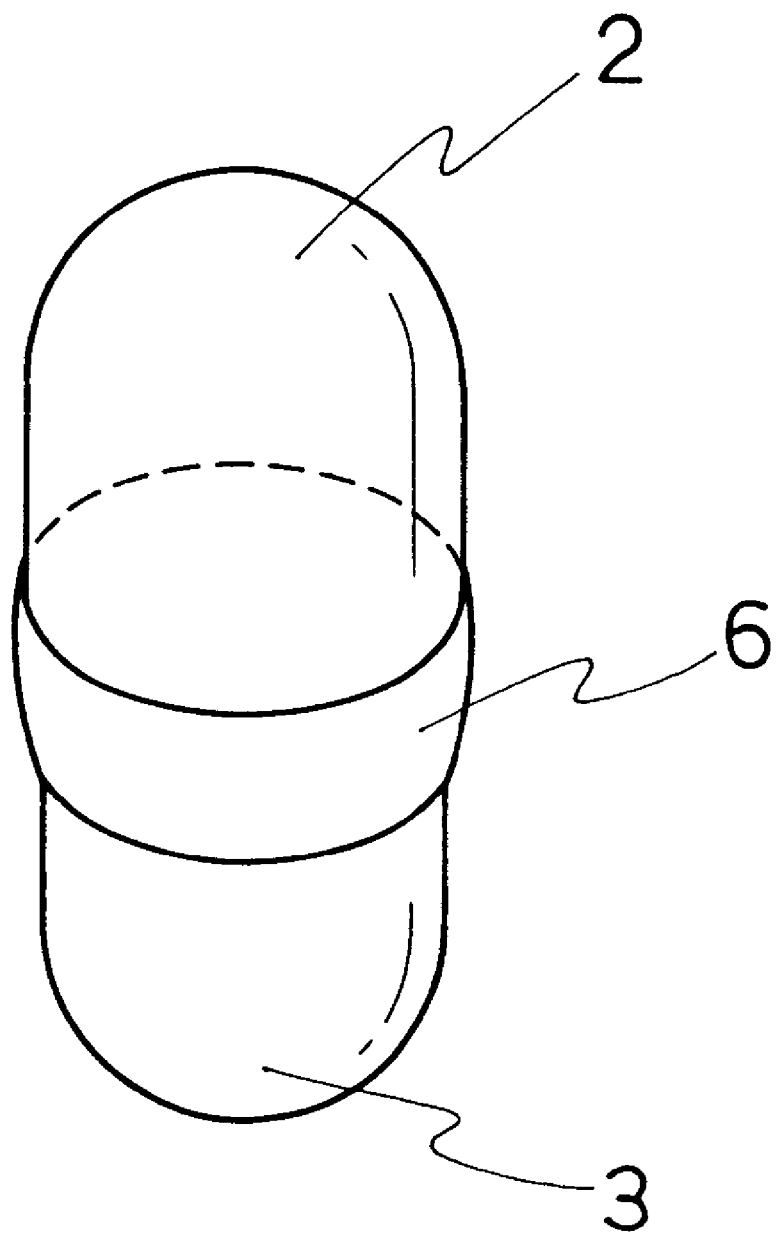
FIG. 4 shows a perspective view of a hard capsule with a sealing means around the joint thereof.

FIG. 4 shows a perspective view of a hard capsule with a sealing means around the joint 8 of the body 3 and the cap 2 thereof.

Preferred embodiments of the pharmaceutical preparation of the present invention are given below.

(1) The kind of and the amount of polymer(s) used for the low pH-soluble polymer film and the kind of the acidic substance are selected so that contents of a hard capsule can be released at any desired site of the lower part of the digestive tract;

(2) The kind of and the amount of polymer(s) used for the low pH-soluble polymer film and the kind of the acidic substance are selected so that contents of a hard capsule can be released at any desired site between the jejunum and the rectum;

(3) The kind of and the amount of polymer(s) used for the low pH-soluble polymer film and the kind of the acidic substance are selected so that contents of a hard capsule can be released at any desired site between the ileum and the rectum;

(4) The kind of and the amount of polymer(s) used for the low pH-soluble polymer film and the kind of the acidic substance are selected so that contents of a hard capsule can be released at any desired site of the large intestine;

(5) The kinds of and the amount of polymer(s) used for the low pH-soluble polymer film and the kind of the acidic substance are determined so that contents of a hard capsule can be released after the desired time period when a dissolution test is carried out with the JP 2nd-Fluid according to the disintegration test described in JP XII;

(6) The acidic substance is an organic acid;

(7) The acidic substance is at least one member selected from the group consisting of succinic acid, maleic acid, tartaric acid, citric acid, fumaric acid and malic acid;

(8) The hard capsule is commercially available;

(9) The hard capsule is a gelatin capsule, a corn starch capsule or a hydroxypropylmethylcellulose capsule;

(10) The hard capsule is a gelatin capsule or a hydroxypropylmethylcellulose capsule;

(11) The hard capsule is a gelatin capsule;

(12) The low pH-soluble polymer film comprises a film-formable polymeric substance which is soluble at an acidic range of from pH 1 to pH 5 but not soluble at a neutral and alkaline range of a pH of higher than 5;

(13) The low pH-soluble polymer film comprises at least one member selected from the group consisting of polyvinylacetal diethylaminoacetate and methyl methacrylate-butyl methacrylate-dimethyl methacrylate copolymer;

(14) The enteric coating film comprises a film-formable polymeric substance which is soluble in an aqueous medium having a pH of higher than 5 but not soluble in an aqueous medium of a pH of at most 5;

(15) The enteric coating film comprises at least one member selected from the group consisting of a cellulose derivative, shellac, an acrylic copolymer, a maleic copolymer and a polyvinyl derivative; and

(16) The enteric coating film comprises at least one member selected from the group consisting of hydroxypropylmethylcellulose acetate succinate, hydroxypropylmethylcellulose phthalate, carboxymethylethylcellulose and methacrylic acid-methyl methacrylate copolymer;

The present invention is more specifically described and explained by means of the following Examples and Experimental Examples.

Experimental Example 1

(1) Dissolution Test

With respect to the pharmaceutical preparation containing prednisolone obtained in the following Example 1, a dissolution test was carried out with the JP 1st-Fluid of the disintegration test in JP XII (pH 1.2, hereinafter referred to as the JP 1st-Fluid) and the JP 2nd-Fluid of the disintegration test in JP XII (pH 6.8, hereinafter referred to as the JP 2nd-Fluid), using 900 ml of the dissolution fluid at 37° C. and at the rotation speed of 100 rpm according to the paddle method based on the specification of the dissolution test described in JP XII.

Figure 5:
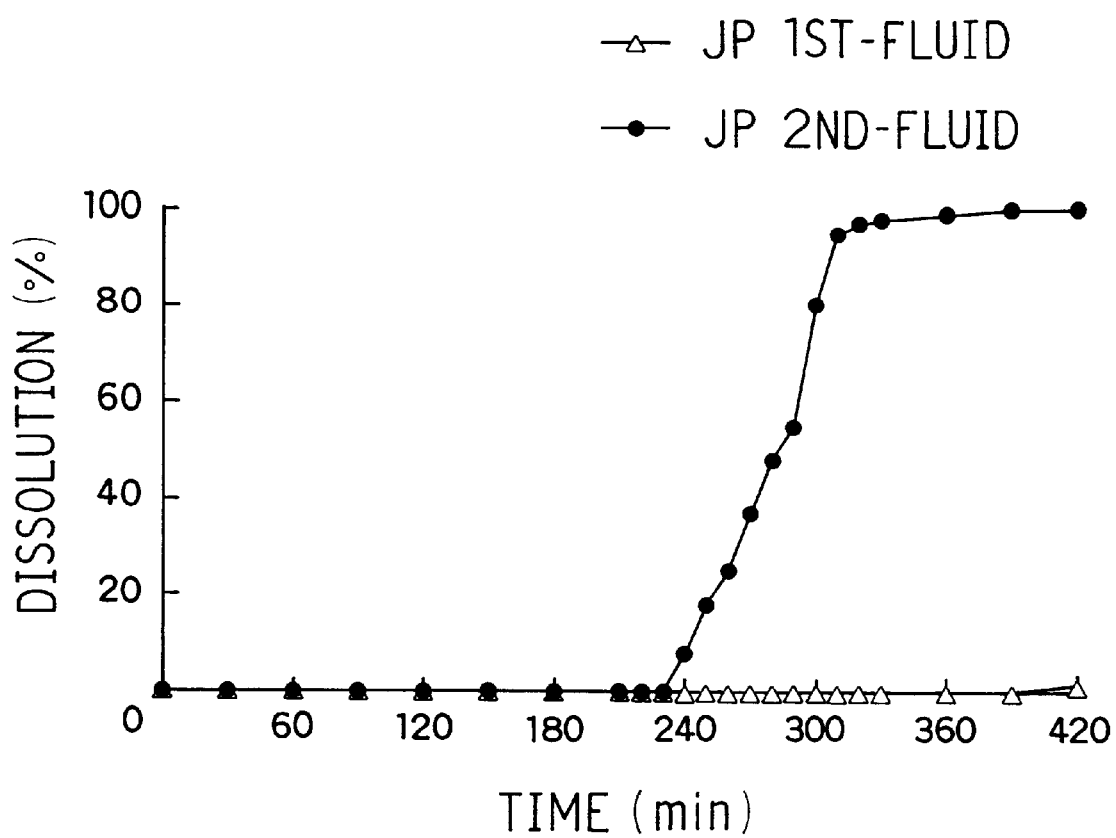
FIG. 5 is a graph showing the result of the dissolution test with the JP 1st-Fluid and the JP 2nd-Fluid as to a pharmaceutical preparation of the present invention in Experimental Example 1. The term "JP" means the 12th Japanese Pharmacopoeia

The results of the dissolution test are shown in FIG. 5. With respect to the pharmaceutical preparation of the present invention, the medicament was not dissolved at all for a long time in the the JP 1st-Fluid, which means that the acid resistance of the pharmaceutical preparation was maintained sufficiently.

In the JP 2nd-Fluid, the medicament was quickly dissolved after the lag-time of about 4 hours and it is seen that it takes about 1 hour after the start of dissolution to dissolve 80% of the medicament.

(2) In vivo Absorption Test

In the course of preparing the above-mentioned pharmaceutical preparation, an intermediate layer was provided between the Eudragit E100 layer and the hydroxypropylmethylcellulose acetate succinate layer by coating the Eudragit E100 layer with theophylline as an indicator of gastric emptying in a coating amount of 20 mg per capsule. Thus a pharmaceutical preparation having an intermediate layer in the pharmaceutical preparation of the Experimental Example 1(1) was obtained.

Into each of three beagle dogs weighing 9 to 12 kg which had fasted a day and night, tetragastrin (10 μg/kg body weight) was intramuscularly injected. Ninety minutes after the injection, one of the pharmaceutical preparation containing 10 mg of prednisolone and 20 mg of theophylline as the gastric emptying indicator obtained in the above was orally administered to each beagle dog together with 50 ml of purified water. After administration, the blood was collected at predetermined times and the concentration (μg/ml) of prednisolone and theophilline in the plasma was determined.

Figure 6:
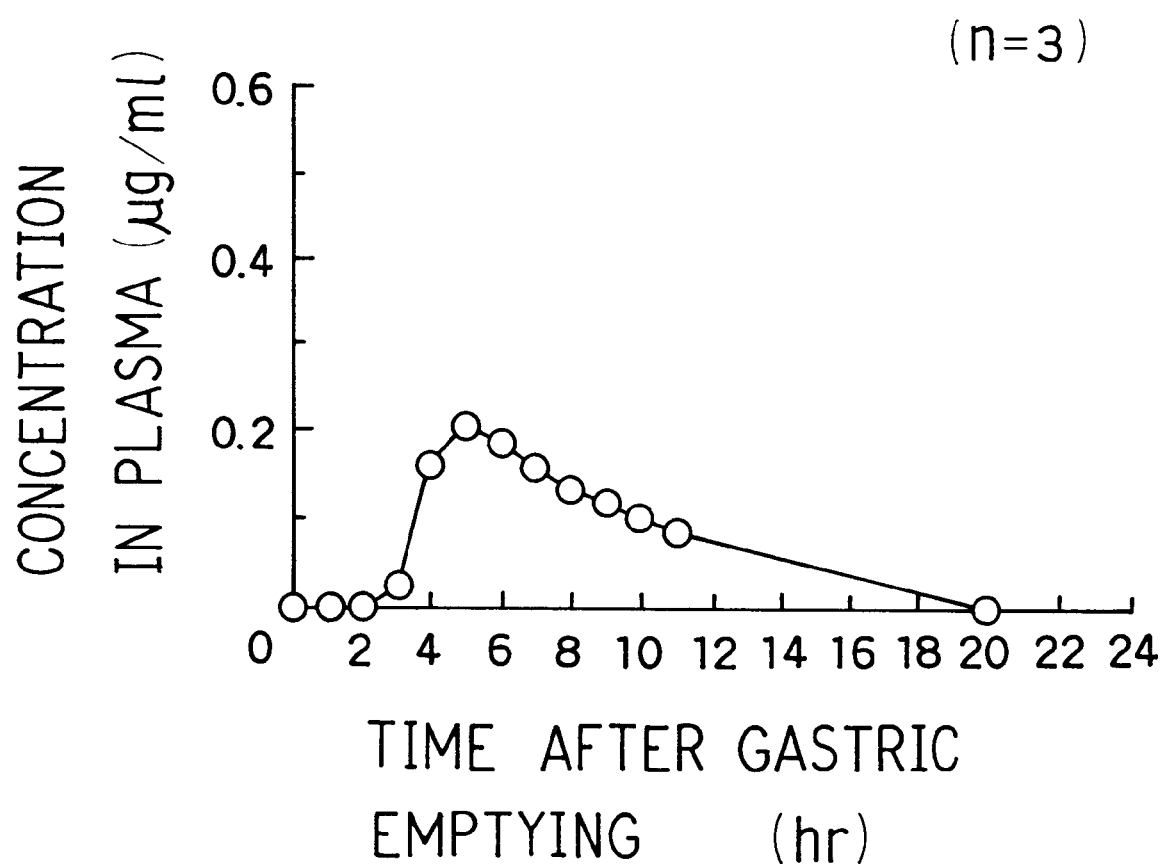
FIG. 6 is a graph showing the change of the concentration of a medicament in the plasma in the case that the pharmaceutical preparation of the present invention was administered to dogs in Experimental Example 1.

The change of the concentration of prednisolone in the plasma is shown in FIG. 6 using the mean of the determined three concentrations. The concentration of the medicament in the plasma quickly increased from about 3 hours after the gastric emptying and reached a maximum about 5 hours after the gastric emptying. These results suggest that in the pharmaceutical preparation of the present invention, a medicament is released and then satisfactorily absorbed.

Experimental Example 2
(1) Preparation Method

A white hard gelatin capsule of Size No. 2 (commercially available from CAPSUGEL AG, Japan) was filled with a mixture of 20 mg of theophylline and 100 mg of succinic acid to obtain a core capsule.

The core capsule was spray-coated with a 5% by weight coating solution of Eudragit E100 (trade name, methyl methacrylate-butyl methacrylate-dimethylaminoethyl methacrylate copolymer, commercially available from Röhm Pharma, Germany) dissolved in ethanol, in a coating amount of 20, 30, 40, 50, 60, 70, 80, 90 or 100 mg per capsule as Eudragit E100 by means of HICOATER (trade name, made by Freund Industrial Co., Ltd., Japan) to obtain nine kinds of capsules coated with a low pH-soluble polymer film, which differed from each other in the amount of the low pH-soluble polymer film.

(2) Dissolution Test

With respect to each of nine kinds of the preparations obtained in the above (1), the dissolution test was carried out with the JP 2nd-Fluid under the same conditions as in Experimental Example 1(1).

Figure 7:
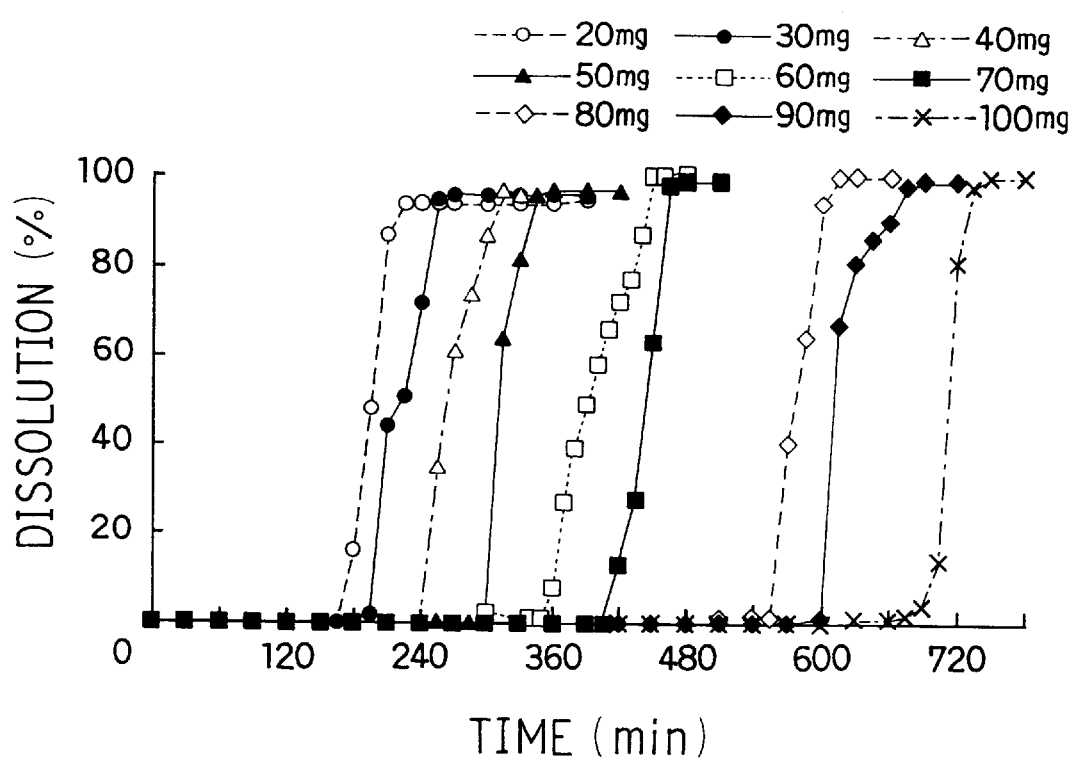
FIG. 7 is a graph showing the results of the dissolution test with the JP 2nd-Fluid as to preparations in the form of a capsule coated with Eudragit E100 which are different in the coating amount of Eudragit E100, in Experimental Example 2.
Figure 8:
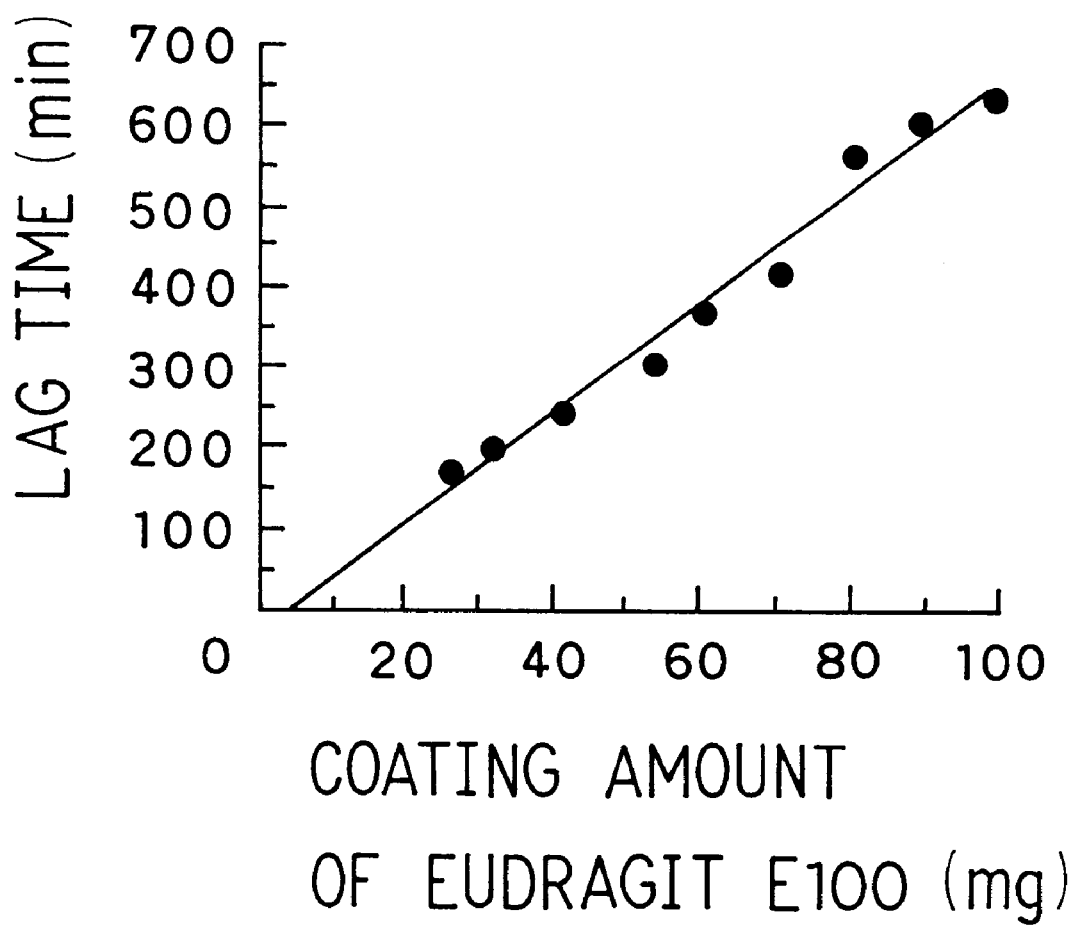
FIG. 8 is a graph showing relationship between the coating amount of Eudragit E100 and the lag-time.

The results of the dissolution test are shown in FIG. 7. FIG. 8 shows the relationship between the lag-time and the coating amount of Eudragit E100, which was based on the results of the dissolution test. It is understood that according to the pharmaceutical preparation of the present invention, a lag-time can be easily and widely controlled by the amount of the low pH-soluble polymer film. In addition, it is understood that in each preparation, it takes about 1 hour after each start of dissolution to dissolve 80% of the medicament and therefore the increase of the amount of the low pH-soluble polymer film does not influence the dissolution rate of the medicament.

Experimental Example 3
(1) Preparation Method

Each white hard gelatin capsule of Size No. 2 (commercially available from CAPSUGEL AG, Japan) was filled with a mixture of 20 mg of theophylline and 100 mg of maleic acid, tartaric acid, fumaric acid or citric acid to obtain four kinds of core capsules. To each of the core capsules, a sealing means (1.5% by weight, based on the weight of the used empty hard capsule) was provided around the joint of the body and the cap of the core capsule by applying a 10% by weight solution of ethylcellulose in ethanol on the joint using a Pasteur pipet and by drying using a dryer to seal the joint.

The obtained core capsule with a sealing means was subjected to the same procedure as in the following Example 1(2). Thus there were obtained four kinds of capsules coated with a low pH-soluble polymer film, which differed from each other in the kind of the acidic substance.

(2) Dissolution Test

With respect to each of four kinds of the preparations obtained in the above (1), the dissolution test was carried out with the JP 2nd-Fluid under the same conditions as in Experimental Example 1(1).

Figure 9:
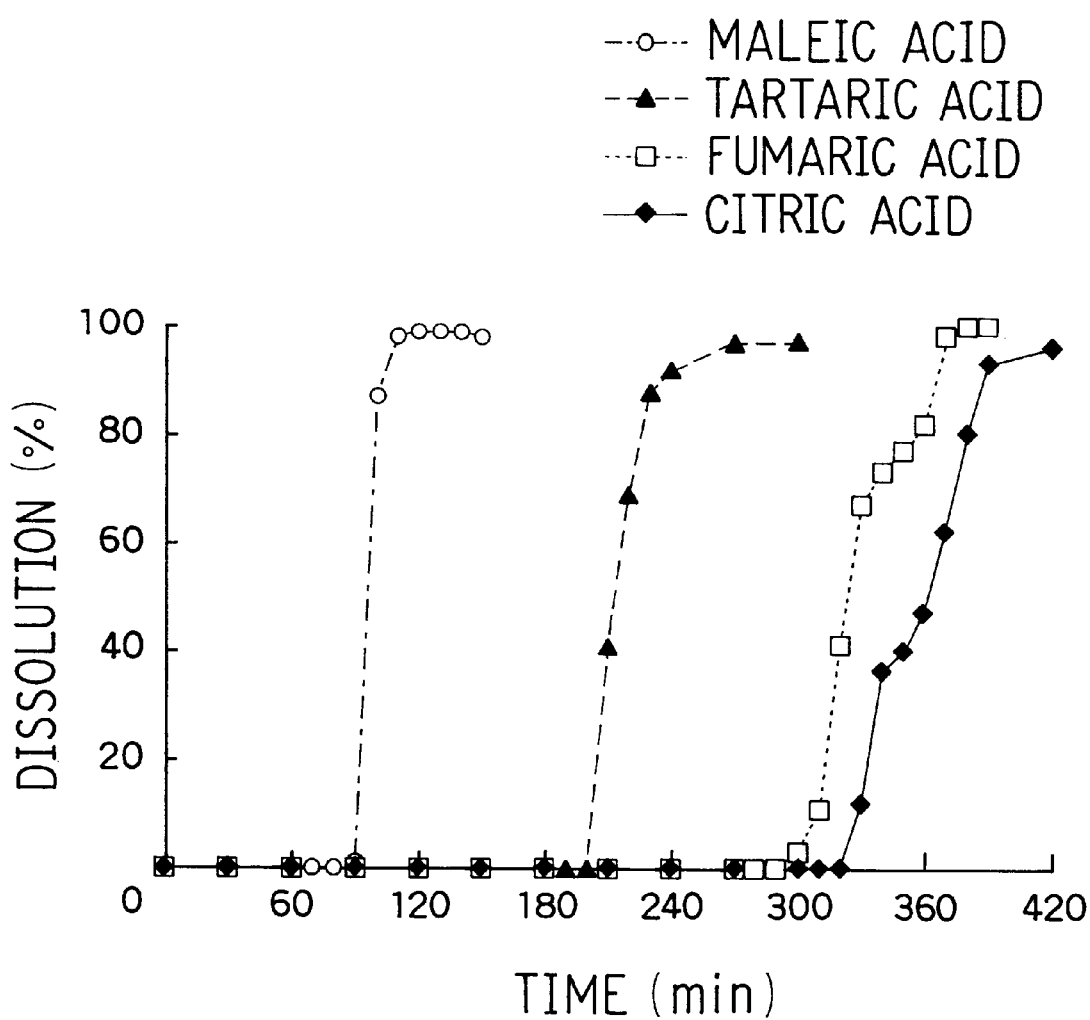
FIG. 9 is a graph showing the results of the dissolution test with the JP 2nd-Fluid as to preparations in the form of a capsule coated with Eudragit E100 which are different in the kind of an acidic substance, in Experimental Example 3.

The results of the dissolution test are shown in FIG. 9. It is understood that according to the pharmaceutical preparation of the present invention, a lag-time can be controlled by changing the kind of the acidic substance. In addition, it is understood that in each preparation, it takes about 1 hour after the start of release to release 80% of the medicament, and therefore the kind of the acidic substance does not influence the dissolution rate of the medicament.

Experimental Example 4
(1) Preparation Method

A white hard gelatin capsule of Size No. 2 (commercially available from CAPSUGEL AG, Japan) was filled with a mixture of 20 mg of theophylline and 0, 10, 20, 50 or 100 mg of succinic acid to obtain five kinds of core capsules.

The core capsules were subjected to the same procedures as in the following Example 1(2) and 1(3) to obtain five kinds of pharmaceutical preparations of the present invention, which differed from each other in the amount of the acidic substance.

(2) Dissolution Test

With respect to each of five kinds of the pharmaceutical preparations obtained in the above (1), the dissolution test was carried out with the JP 2nd-Fluid under the same conditions as in Experimental Example 1(1).

Figure 10:
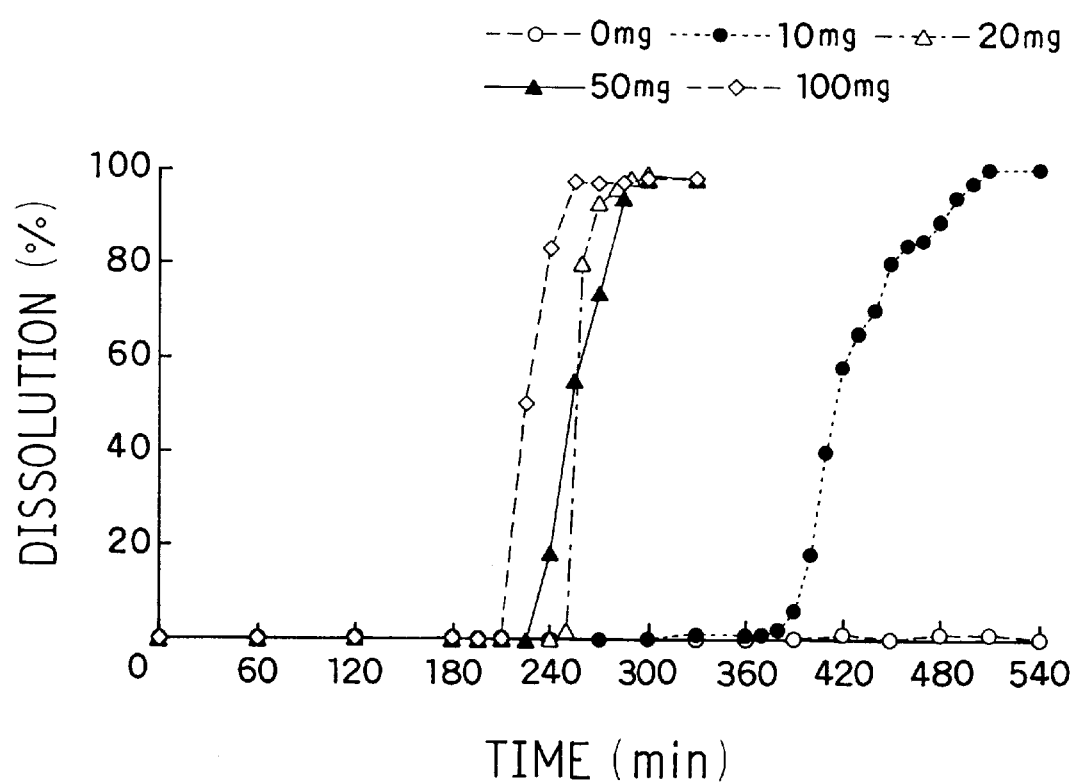
FIG. 10 is a graph showing the results of the dissolution test with the JP 2nd-Fluid as to pharmaceutical preparations of the present invention which are different in the amount of succinic acid, in Experimental Example 4.

The results of the dissolution test are shown in FIG. 10. It is understood that the lag-time and the dissolution rate of a medicament are hardly influenced by the amount of succinic acid when the amount of succinic acid per a capsule becomes at least about 20 mg.

Experimental Example 5
Dissolution Test

With respect to the pharmaceutical preparations (n=6) wherein a sealing means is provided, obtained in the following Example 2, the dissolution test was carried out with the JP 2nd-Fluid under the same condition as in Experimental Example 1(1).

Figure 11:
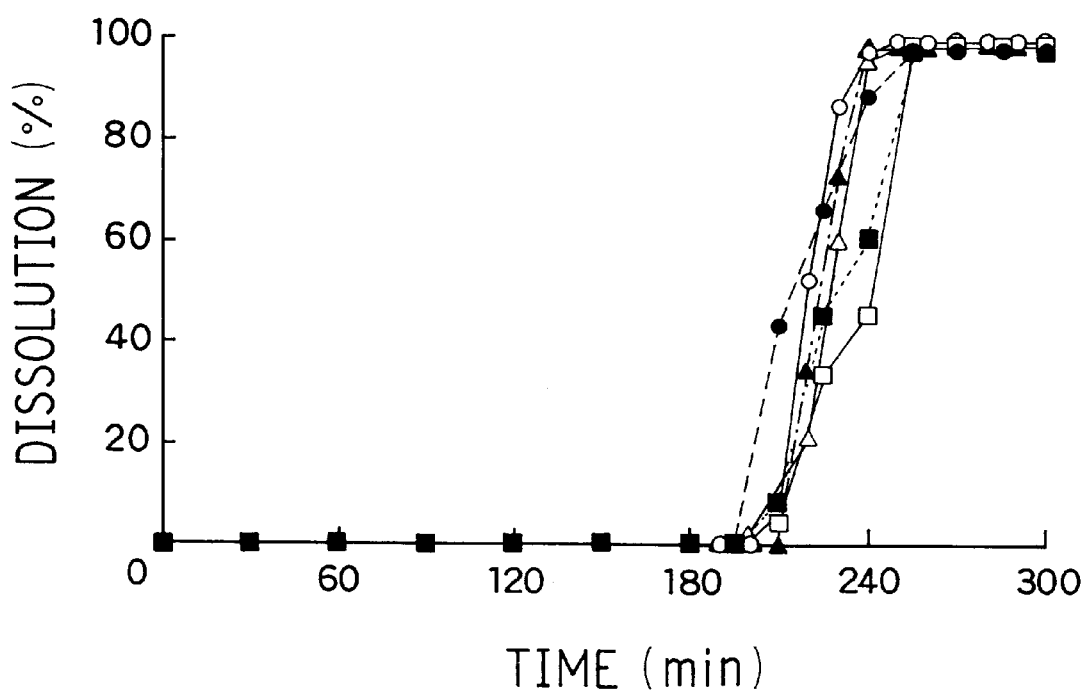
FIG. 11 is a graph showing the results of the dissolution test with the JP 2nd-Fluid as to pharmaceutical preparations of the present invention wherein a sealing means is provided, in Experimental Example 5.

The results of the dissolution test are shown in FIG. 11. It is understood that the pharmaceutical preparation of the present invention wherein a sealing means is provided around the joint of the body and the cap of the capsule is excellent because of having quite little deviation of the dissolution pattern.

EXAMPLE 1

(1) A white hard gelatin capsule of Size No. 2 (63 mg) (commercially available from CAPSUGEL AG, Japan) was filled with a mixture of 10 mg of prednisolone and 100 mg of succinic acid to obtain a core capsule.

(2) The core capsule was spray-coated with a 5% by weight solution of Eudragit E100 (trade name, methyl methacrylate-butyl methacrylate-dimethylaminoethyl methacrylate copolymer, commercially available from Röhm Pharma, Germany) dissolved in ethanol, in a coating amount of 30 mg per capsule (48% by weight, based on the weight of the used empty hard capsule) as Eudragit E100 by means of HICOATER (trade name, made by Freund Industrial Co., Ltd., Tokyo, Japan, hereinafter the same) to obtain a capsule coated with a low pH-soluble polymer film.

(3) Thus obtained coated capsule was further spray-coated with a coating solution, which was prepared by dissolving HPMC-AS (trade name, hydroxypropylmethylcellulose acetate succinate, commercially available from Shin-Etsu Chemical Co., Ltd., Japan) in a mixture of ethanol and water (5:3 (w/w)) to obtain a 5% by weight HPMC-AS solution and adding thereto talc in an amount of 2.5% by weight, based on the total weight of the 5% HPMC-AS solution, in a coating amount of 100 mg per capsule (159% by weight, based on the weight of the used empty hard capsule) as HPMC-AS by means of HICOATER.

Thus a pharmaceutical preparation of the present invention was obtained in the form of a coated capsule releasable at the lower part of the digestive tract.

EXAMPLE 2

(1) A white hard gelatin capsule of Size No. 2 (commercially available from CAPSUGEL AG, Japan) was filled with a mixture of 20 mg of theophylline and 100 mg of succinic acid to obtain a core capsule. To the joint of the body and the cap of the core capsule, a sealing means (1.5% by weight, based on the weight of the used empty hard capsule) was provided by applying a 10% by weight solution of ethylcellulose in ethanol using a Pasteur pipet and by drying using a dryer to seal the joint.

(2) The obtained core capsule with a sealing means was subjected to the same procedures as in Example 1(2) and 1(3) to obtain a pharmaceutical preparation of the present invention wherein a sealing means is provided around the joint of the hard capsule.

EXAMPLE 3

(1) A white hard gelatin capsule of Size No. 2 (commercially available from CAPSUGEL AG, Japan) was filled with a mixture of 10 mg of prednisolone and 100 mg of succinic acid to obtain a core capsule. To the joint of the body and the cap, a sealing means (1.5% by weight, based on the weight of the used empty hard capsule) was provided by applying a 10% by weight solution of ethylcellulose in ethanol using a Pasteur pipet and by drying using a dryer to seal the joint.

(2) The obtained core capsule with a sealing means was subjected to the same procedure as in Example 1(2) to obtain a capsule coated with a low pH-soluble polymer film.

(3) Thus obtained coated capsule was further spray-coated with a 5% by weight aqueous solution of TC-5 (trade name, hydroxypropylmethylcellulose, commercially available from Shin-Etsu Chemical Co., Ltd., Japan) in a coating amount of 15 mg per capsule (24% by weight, based on the weight of the used empty hard capsule) by means of HICOATER to obtain a double-coated capsule wherein the low pH-soluble polymer film is further coated with an intermediate layer.

(4) Thus obtained double-coated capsule was subjected to the same procedure as in Example 1(3) to obtain a pharmaceutical preparation of the present invention wherein a sealing means and an intermediate layer are provided.

EXAMPLE 4

(1) A white hard gelatin capsule of Size No. 2 (commercially available from CAPSUGEL AG, Japan) was filled with a mixture of 20 mg of theophylline and 100 mg of tartaric acid to obtain a core capsule.

(2) The obtained core capsule was subjected to the same procedures as in Example 1(2) and 1(3) to obtain a pharmaceutical preparation of the present invention.

EXAMPLE 5

(1) A white hard HPMC capsule of Size No. 2 (commercially available from Japan Elanco CO., LTD., Japan) was filled with a mixture of 20 mg of theophylline and 100 mg of succinic acid to obtain a core capsule.

(2) The obtained core capsule was subjected to the same procedures as in Example 1(2) and 1(3) to obtain a pharmaceutical preparation of the present invention.

EXAMPLE 6

(1) A white hard gelatin capsule of Size No. 2 (commercially available from CAPSUGEL AG, Japan) was filled with a mixture of 20 mg of theophylline and 100 mg of maleic acid to obtain a core capsule.

(2) The obtained core capsule was subjected to the same procedures as in Example 1(2) and 1(3) to obtain a pharmaceutical preparation of the present invention.

EXAMPLE 7

(1) A white hard gelatin capsule of Size No. 2 (commercially available from CAPSUGEL AG, Japan) was filled with a mixture of 20 mg of theophylline and 100 mg of citric acid to obtain a core capsule.

(2) The obtained core capsule was subjected to the same procedures as in Example 1(2) and 1(3) to obtain a pharmaceutical preparation of the present invention.

EXAMPLE 8

(1) A white hard gelatin capsule of Size No. 2 (commercially available from CAPSUGEL AG, Japan) was filled with a mixture of 20 mg of theophylline and 100 mg of fumaric acid to obtain a core capsule.

(2) The obtained core capsule was subjected to the same procedures as in Example 1(2) and 1(3) to obtain a pharmaceutical preparation of the present invention.

EXAMPLE 9

(1) A white hard gelatin capsule of Size No. 2 (commercially available from CAPSUGEL AG, Japan) was filled with a mixture of 20 mg of theophylline and 100 mg of malic acid to obtain a core capsule.

(2) The obtained core capsule was subjected to the same procedures as in Example 1(2) and 1(3) to obtain a pharmaceutical preparation of the present invention.

EXAMPLE 10

(1) A white hard gelatin capsule of Size No. 2 (commercially available from CAPSUGEL AG, Japan) was filled with a mixture of 20 mg of theophylline and 100 mg of succinic acid to obtain a core capsule.

(2) The core capsule was spray-coated with a 5% by weight solution of polyvinylacetal diethylaminoacetate in ethanol in a coating amount of 30 mg per capsule (48% by weight, based on the weight of the used empty hard capsule) as polyvinylacetal diethylaminoacetate by means of HICOATER to obtain a capsule coated with a low pH-soluble polymer film.

(3) Thus obtained coated capsule was subjected to the same procedure as in Example 1(3) to obtain a pharmaceutical preparation of the present invention.

EXAMPLE 11

(1) A white hard gelatin capsule of Size No. 2 (commercially available from CAPSUGEL AG, Japan) was filled with a mixture of 10 mg of prednisolone and 100 mg of succinic acid to obtain a core capsule.

(2) The core capsule was subjected to the same procedure as in Example 1(2) to obtain a capsule coated with a low pH-soluble polymer film.

(3) Thus obtained coated capsule was further spray-coated with a coating solution, which was prepared by dissolving hydroxypropylmethylcellulose phthalate in a mixture of ethanol and water (8:2 (w/w)) to obtain a 5% by weight solution of hydroxypropylmethylcellulose phthalate and adding thereto talc in an amount of 2.5% by weight, based on the total weight of the 5% solution, in a coating amount of 80 mg per capsule (127% by weight, based on the weight of the used empty hard capsule) as hydroxypropylmethylcellulose phthalate by means of HICOATER.

Thus a pharmaceutical preparation of the present invention was obtained in the form of a coated capsule releasable at the lower part of the digestive tract.

EXAMPLE 12

(1) A white hard gelatin capsule of Size No. 2 (commercially available from CAPSUGEL AG, Japan) was filled with a mixture of 10 mg of prednisolone and 100 mg of succinic acid to obtain a core capsule.

(2) The core capsule was subjected to the same procedure as in Example 1(2) to obtain a capsule coated with a low pH-soluble polymer film.

(3) Thus obtained coated capsule was further spray-coated with a coating solution, which was prepared by dissolving cellulose acetate phthalate in a mixture of ethanol and water (8:2 (w/w)) to obtain a 5% by weight solution of cellulose acetate phthalate and adding thereto talc in an amount of 5% by weight, based on the total weight of the 5% solution, in a coating amount of 100 mg per capsule (159% by weight, based on the weight of the used empty hard capsule) as cellulose acetate phthalate by means of HICOATER.

Thus a pharmaceutical preparation of the present invention was obtained in the form of a coated capsule releasable at the lower part of the digestive tract.

EXAMPLE 13

(1) A white hard gelatin capsule of Size No. 2 (commercially available from CAPSUGEL AG, Japan) was filled with a mixture of 10 mg of prednisolone and 100 mg of succinic acid to obtain a core capsule.

(2) The core capsule was subjected to the same procedure as in Example 1(2) to obtain a capsule coated with a low pH-soluble polymer film.

(3) Thus obtained coated capsule was further spray-coated with a coating solution, which was prepared by dissolving Eudragit L100 (trade name, methacrylic acid-methyl methacrylate copolymer, commercially available from Röhm Pharma, Germany) in a mixture of ethanol and water (8:2 (w/w)) to obtain a 5% by weight solution of Eudragit L100 and adding thereto talc in an amount of 5% by weight, based on the total weight of the 5% Eudragit L100 solution, in a coating amount of 80 mg per capsule (127% by weight, based on the weight of the used empty hard capsule) as Eudragit L100 by means of HICOATER Thus a pharmaceutical preparation of the present invention was obtained in the form of a coated capsule releasable at the lower part of the digestive tract.

EXAMPLE 14

(1) A white hard gelatin capsule of Size No. 2 (commercially available from CAPSUGEL AG, Japan) was filled with a mixture of 10 mg of prednisolone and 100 mg of succinic acid to obtain a core capsule.

(2) The core capsule was subjected to the same procedure as in Example 1(2) to obtain a capsule coated with a low pH-soluble polymer layer.

(3) Thus obtained coated capsule was further spray-coated with a coating solution, which was prepared by dissolving Eudragit S100 (trade name, methacrylic acid-methyl methacrylate copolymer, commercially available from Röhm Pharma, Germany) in a mixture of ethanol and water (8:2 (w/w)) to obtain a 5% by weight solution of Eudragit S100 and adding thereto talc in an amount of 5% by weight, based on the total weight of the 5% Eudragit S100 solution, in a coating amount of 90 mg per capsule (143% by weight, based on the weight of the used empty hard capsule) as Eudragit S100 by means of HICOATER.

Thus a pharmaceutical preparation of the present invention was obtained in the form of a coated capsule releasable at the lower part of the digestive tract.

EXAMPLE 15

(1) A white hard gelatin capsule of Size No. 2 (commercially available from CAPSUGEL AG, Japan) was filled with a mixture of 10 mg of prednisolone and 100 mg of succinic acid to obtain a core capsule.

(2) The core capsule was subjected to the same procedure as in Example 1(2) to obtain a capsule coated with a low pH-soluble polymer film.

(3) Thus obtained coated capsule was further spray-coated with a coating solution, which was prepared by dissolving Eudragit L100-55 (trade name, methacrylic acid-ethyl acrylate copolymer, commercially available from Röhm Pharma, Germany) in a mixture of ethanol and water (8:2 (w/w)) to obtain a 5% by weight solution of Eudragit L100-55 and adding thereto talc in an amount of 5% by weight, based on the total weight of the 5% solution of Eudragit L100-55, in a coating amount of 100 mg per capsule (159% by weight, based on the weight of the used empty hard capsule) as Eudragit L100-55 by means of HICOATER.

Thus a pharmaceutical preparation of the present invention was obtained in the form of a coated capsule releasable at the lower part of the digestive tract.

In addition to the ingredients used in the Examples, other ingredients can be used in the Examples as set forth in the specification to obtain substantially the same results.

What is claimed is:

1. A pharmaceutical preparation in the form of a coated capsule which can release contents of a capsule at a lower part of the digestive tract comprising
   (a) a hard capsule containing an acidic substance to control release of the contents of the capsule and at least one member selected from the group consisting of a medicament, a pharmaceutical preparation and a functional substance,
   (b) a polymer film soluble at low pH which is formed on a surface of said hard capsule, and
   (c) an enteric coating film which is formed on a surface of said polymer film soluble at low pH.

2. pharmaceutical preparation in the form of a coated capsule which can release contents of a capsule at a lower part of the digestive tract comprising
   (a) a hard capsule containing at least an acidic substance to control release of the contents of the capsule,
   (b) a polymer film soluble at low pH which is formed of a surface of said hard capsule, (c) an enteric coating film which is formed on a surface of said polymer film soluble at low pH, and (d) at least one of
(1) a sealing means provided around a joint of a body and a cap of said hard capsule, and
(2) an intermediate layer comprising at least one member selected from the group consisting of a medicament and a water-soluble substance between said polymer film soluble at low pH and said enteric coating film.

3. The pharmaceutical preparation of claim 1 wherein a sealing means is provided around a joint of a body and a cap of said hard capsule.

4. A pharmaceutical preparation in the form of a coated capsule which can release contents of a capsule at a lower part of the digestive tract comprising (a) a hard capsule containing at least an acidic substance, (b) a polymer film soluble at low pH which is formed on a surface of said hard capsule, and (c) an enteric coating film which is formed on a surface of said polymer film soluble at low pH, wherein said acidic substance is a solid substance of which aqueous solution has pH value of at most 5.

5. The pharmaceutical preparation of claim 1 wherein said acidic substance is at least one member selected from the group consisting of an organic acid and an inorganic acid.

6. The pharmaceutical preparation of claim 1 wherein said polymer film soluble at low pH comprises at least one member selected from the group consisting of polyvinyl acetal diethylaminoacetate, methyl methacrylate-butyl methacrylate-dimethylaminoethyl methacrylate copolymer and polyvinyl aminoacetal.

7. The pharmaceutical preparation of claim 1 wherein said enteric coating film comprises at least one member selected from the group consisting of hydroxypropylmethylcellulose acetate succinate, hydroxypropylmethylcellulose phthalate, hydroxymethylethylcellulose phthalate, cellulose acetate phthalate, cellulose acetate succinate, cellulose acetate malate, cellulose benzoate phthalate, cellulose propionate phthalate, methylcellulose phthalate, carboxymethylethylcellulose, ethylhydroxyethylcellulose phthalate, shellac, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer, methacrylic acid-ethyl acrylate copolymer, methyl acrylate-methacrylic acid-octyl acrylate copolymer, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer, polyvinyl alcohol phthalate, polyvinyl acetal phthalate, polyvinyl butylate phthalate and polyvinyl acetoacetal phthalate.

8. The pharmaceutical preparation of claim 1 wherein an intermediate layer comprising at least one member selected from the group consisting of a medicament and a water-soluble substance is provided between said polymer film soluble at low pH and said enteric coating film.

9. A pharmaceutical preparation in the form of a coated capsule which can release contents of a capsule in a lower part of the digestive tract, consisting essentially of:

(a) a core in the form of a hard capsule containing an active agent and a solid acidic substance, and having an outer surface, (b) a polymer film soluble at low pH which is formed on said outer surface of said hard capsule, (c) optionally an intermediate layer selected from the group consisting of at least one of a medicament and a water-soluble substance formed on an outer surface of said polymer film soluble at low pH, and (d) an enteric coating film which is formed on an outer surface of said intermediate layer if present or on an outer surface of said polymer film soluble at low pH if said intermediate film is not present.

10. A pharmaceutical preparation according to claim 9, wherein said optional intermediate layer is present.

11. A pharmaceutical preparation according to claim 9, wherein said optional intermediate layer is not present.

12. A pharmaceutical preparation in the form of a coated capsule which can release contents of a capsule at a lower part of the digestive tract comprising (a) a hard capsule containing at least an acidic substance to control release of the contents of the capsule, (b) a polymer film soluble at low pH which is formed on a surface of said hard capsule, and (c) an enteric coating film which is formed on a surface of said polymer film soluble at low pH, and wherein
(1) said acidic substance is at least one member selected from the group consisting of an organic acid and an inorganic acid,
(2) said polymer film soluble at low pH comprises at least one member selected from the group consisting of polyvinyl acetal diethylaminoacetate, methyl methacrylate-butyl methacrylate-dimethylaminoethyl methacrylate copolymer and polyvinyl aminoacetal, or
(3) both (1) or (2).

* * * * *